United States Patent

Madin

Patent Number: 6,051,591
Date of Patent: Apr. 18, 2000

[54] DIAZABICYCLOOCTANE DERIVATIVES

[75] Inventor: Andrew Madin, Sawbridgeworth, United Kingdom

[73] Assignee: Merck Sharp & Dohme Ltd., Hertfordshire, United Kingdom

[21] Appl. No.: 09/043,274

[22] PCT Filed: Sep. 19, 1996

[86] PCT No.: PCT/GB96/02312

§ 371 Date: Mar. 12, 1998

§ 102(e) Date: Mar. 12, 1998

[87] PCT Pub. No.: WO97/11949

PCT Pub. Date: Apr. 3, 1997

[30] Foreign Application Priority Data

Sep. 26, 1995 [GB] United Kingdom ............... 9519558

[51] Int. Cl.[7] .................. A61K 31/41; C07D 487/04; C07D 403/14
[52] U.S. Cl. .................................... 514/383; 548/266.4
[58] Field of Search ..................... 548/266.4; 514/383

[56] References Cited

FOREIGN PATENT DOCUMENTS

93/20073  10/1993  WIPO .
96/04274  2/1996  WIPO .

*Primary Examiner*—Patricia L. Morris
*Attorney, Agent, or Firm*—James L. McGinnis; David L. Rose

[57] ABSTRACT

A class of 2,7-diazabicyclo[3.3.0]octane derivatives represented by formula I

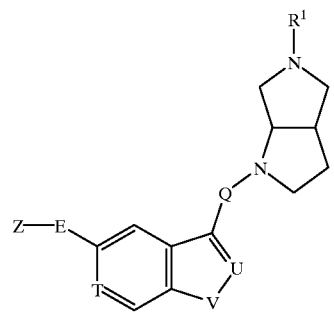

are selective agonists of the $5\text{-}HT_{1D\alpha}$ receptor. The compounds are useful in the treatment of migraine and related conditions.

5 Claims, No Drawings

DIAZABICYCLOOCTANE DERIVATIVES

The present invention relates to a class of substituted 2,7-diazabicyclo[3.3.0]octane derivatives which act on 5-hydroxytryptamine (5-HT) receptors, being selective agonists of so-called "5-HT$_1$-like" receptors. They are therefore useful in the treatment of clinical conditions for which a selective agonist of these receptors is indicated.

It has been known for some time that 5-HT$_1$-like receptor agonists which exhibit selective vasoconstrictor activity are of use in the treatment of migraine (see, for example, A. Doenicke et al., *The Lancet*, 1988, Vol. 1, 1309–11; and W. Feniuk and P. P. A. Humphrey, *Drug Development Research*, 1992, 26, 235–240).

The human 5-HT$_1$-like or 5-HT$_{1D}$ receptor has recently been shown by molecular cloning techniques to exist in two distinct subtypes. These subtypes have been termed 5-HT$_{1D\alpha}$ (or 5-HT$_{1D-1}$) and 5-HT$_{1D\beta}$ (or 5-HT$_{1D-2}$), and their amino acid sequences are disclosed and claimed in WO-A-91/17174.

The 5-HT$_{1D\alpha}$ receptor subtype in humans is believed to reside on sensory terminals in the dura mater. Stimulation of the 5-HT$_{1D\alpha}$ subtype inhibits the release of inflammatory neuropeptides which are thought to contribute to the headache pain of migraine. The human 5-HT$_{1D\beta}$ receptor subtype, meanwhile, is located predominantly on the blood vessels and in the brain, and hence may play a part in mediating constriction of cerebral and coronary arteries, as well as CNS effects.

Administration of the prototypical 5-HT$_{1D}$ agonist sumatriptan (GR43175) to humans is known to give rise at therapeutic doses to certain adverse cardiovascular events (see, for example, F. Willett et al., *Br. Med. J.*, 1992, 304, 1415; J. P. Ottervanger et al., *The Lancet*, 1993, 341, 861–2; and D. N. Bateman, *The Lancet*, 1993, 341, 221–4). Since sumatriptan barely discriminates between the human 5-HT$_{1D\alpha}$ and 5-HT$_{1D\beta}$ receptor subtypes (cf. WO-A-91/17174, Table 1), and since it is the blood vessels with which the 5-HT$_{1D\beta}$ subtype is most closely associated, it is believed that the cardiovascular side-effects observed with sumatriptan can be attributed to stimulation of the 5-HT$_{1D\beta}$ receptor subtype. It is accordingly considered (cf G. W. Rebeck et al., *Proc. Natl. Acad. Sci. USA*, 1994, 91, 3666–9) that compounds which can interact selectively with the 5-HT$_{1D\alpha}$ receptor subtype, whilst having a less pronounced action at the 5-HT$_{1D\beta}$ subtype, might be free from, or at any rate less prone to, the undesirable cardiovascular and other side-effects associated with non-subtype-selective 5-HT$_{1D}$ receptor agonists, whilst at the same time maintaining a beneficial level of anti-migraine activity.

The compounds of the present invention, being selective 5-HT$_1$-like receptor agonists, are accordingly of benefit in the treatment of migraine and associated conditions, e.g. cluster headache, chronic paroxysmal hemicrania, headache associated with vascular disorders, tension headache and paediatric migraine. In particular, the compounds according to this invention are potent agonists of the human 5-HT$_{1D\alpha}$ receptor subtype. Moreover, the compounds in accordance with this invention have been found to possess at least a 10-fold selective affinity for the 5-HT$_{1D\alpha}$ receptor subtype relative to the 5-HT$_{1D\beta}$ subtype, and they can therefore be expected to manifest fewer side-effects than those associated with non-subtype-selective 5-HT$_{1D}$ receptor agonists.

Several distinct classes of substituted five-membered heteroaromatic compounds are described in published European patent applications 0438230, 0494774 and 0497512, and published International patent applications 93/18029, 94/02477 and 94/03446. The compounds described therein are stated to be agonists of 5-HT$_1$-like receptors, and accordingly to be of particular use in the treatment of migraine and associated conditions. None of these publications, however, discloses nor even suggests the 2,7-diazabicyclo[3.3.0] octane derivatives provided by the present invention.

In EP-A-0548813 is described a series of alkoxypyridin-4-yl and alkoxypyrimidin-4-yl derivatives of indol-3-ylalkylpiperazines which are alleged to provide treatment of vascular or vascular-related headaches, including migraine. There is, however, no disclosure nor any suggestion in EP-A-0548813 of replacing the substituted piperazine moiety with a differently substituted 2,7-diazabicyclo[3.3.0] octane moiety.

WO-A-91/18897 describes a class of tryptamine derivatives substituted by various five-membered rings, which are stated to be specific to a particular type of "5-HT$_1$-like" receptor and thus to be effective agents for the treatment of clinical conditions, particularly migraine, requiring this activity. However, WO-A-91/18897 neither discloses nor suggests the 2,7-diazabicyclo[3.3.0]octane derivatives provided by the present invention.

Moreover, nowhere in the prior art mentioned above is there any disclosure of a subtype-selective 5-HT$_{1D}$ receptor agonist having a 5-HT$_{1D\alpha}$ receptor binding affinity (IC$_{50}$) below 50 nM and at least a 10-fold selective affinity for the 5-HT$_{1D\alpha}$ receptor subtype relative to the 5-HT$_{1D\beta}$ subtype.

The compounds according to the present invention are subtype-selective 5-HT$_{1D}$ receptor agonists having a human 5-HT$_{1D\alpha}$ receptor binding affinity (IC$_{50}$) below 50 nM, typically below 10 nM and preferably below 1 nM; and at least a 10-fold selective affinity, typically at least a 50-fold selective affinity and preferably at least a 100-fold selective affinity, for the human 5-HT$_{1D\alpha}$ receptor subtype relative to the 5-HT$_{1D\beta}$ subtype.

The present invention provides a compound of formula I, or a salt or prodrug thereof:

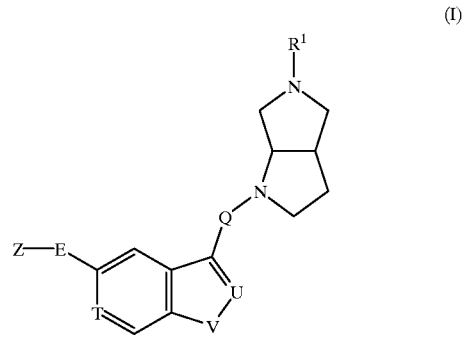

(I)

wherein

Z represents hydrogen, halogen, cyano, nitro, trifluoromethyl, —OR$^5$, —OCOR$^5$, —OCONR$^5$R$^6$, —OCH$_2$CN, —OCH$_2$CONR$^5$R$^6$, —SR$^5$, —SOR$^5$, —SO$_2$R$^5$, —SO$_2$NR$^5$R$^6$, —NR$^5$R$^6$, —NR$^5$COR$^6$, —NR$^5$CO$_2$R$^6$, —NR$^5$SO$_2$R$^6$, —COR$^5$, —CO$_2$R$^5$, —CONR$^5$R$^6$, or a group of formula (a), (b), (c) or (d):

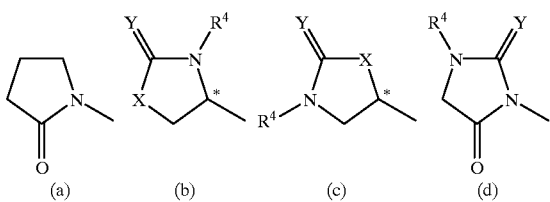

(a)  (b)  (c)  (d)

in which the asterisk * denotes a chiral centre; or

Z represents an optionally substituted five-membered heteroaromatic ring selected from furan, thiophene, pyrrole, oxazole, thiazole, isoxazole, isothiazole, imidazole, pyrazole, oxadiazole, thiadiazole, triazole and tetrazole;

X represents oxygen, sulphur, —NH— or methylene;

Y represents oxygen or sulphur;

E represents a chemical bond or a straight or branched alkylene chain containing from 1 to 4 carbon atoms;

Q represents a straight or branched alkylene chain containing from 1 to 6 carbon atoms, optionally substituted in any position by a hydroxy group;

T represents nitrogen or CH;

U represents nitrogen or C—$R^2$;

V represents oxygen, sulphur or N—$R^3$;

$R^1$ represents $C_{3-6}$ alkenyl, $C_{3-6}$ alkynyl, aryl($C_{1-6}$)alkyl or heteroaryl($C_{1-6}$)alkyl, any of which groups may be optionally substituted;

$R^2$, $R^3$ and $R^4$ independently represent hydrogen or $C_{1-6}$ alkyl; and $R^5$ and $R^6$ independently represent hydrogen, $C_{1-6}$ alkyl, trifluoromethyl, phenyl, methylphenyl, or an optionally substituted aryl($C_{1-6}$)alkyl or heteroaryl($C_{1-6}$)alkyl group.

Where Z in the compounds of formula I above represents a five-membered heteroaromatic ring, this ring may be optionally substituted by one or, where possible, two substituents. As will be appreciated, where Z represents an oxadiazole, thiadiazole or tetrazole ring, only one substituent will be possible; otherwise, one or two optional substituents may be accommodated around the five-membered heteroaromatic ring Z. Examples of suitable substituents on the five-membered heteroaromatic ring Z include $C_{1-6}$ alkyl, $C_{2-6}$ alkenyl, $C_{2-6}$ alkynyl, $C_{3-7}$ cycloalkyl, aryl, aryl($C_{1-6}$) alkyl, $C_{3-7}$ heterocycloalkyl, heteroaryl, heteroaryl($C_{1-6}$) alkyl, $C_{1-6}$ alkoxy, $C_{1-6}$ alkylthio, amino, $C_{1-6}$ alkylanino, di($C_{1-6}$)alkylamino, halogen, cyano and trifluoromethyl.

The group $R^1$ may be optionally substituted by one or more substituents, as also may the groups $R^5$ or $R^6$ where these represent aryl($C_{1-6}$)alkyl or heteroaryl($C_{1-6}$)alkyl. Where $R^1$, $R^5$ or $R^6$ represents aryl($C_{1-6}$)alkyl or heteroaryl ($C_{1-6}$)alkyl, any optional substitution will suitably be on the aryl or heteroaryl moiety thereof, although substitution on the alkyl moiety thereof is an alternative possibility. Examples of optional substituents thereon include halogen, cyano, trifluoromethyl, triazolyl, tetrazolyl, $C_{1-6}$ alkyltetrazolyl, hydroxy, $C_{1-6}$ alkoxy, $C_{1-6}$ alkylthio, $C_{2-6}$ alkoxycarbonyl, $C_{2-6}$ alkylcarbonyl, $C_{1-6}$ alkylsulphonyl, arylsulphonyl, amino, $C_{1-6}$ alkylamino, di($C_{1-6}$)alkylario, di($C_{1-6}$)alkylaminomethyl, $C_{2-6}$ alkylcarbonylamino, arylcarbonylamino, $C_{2-6}$ alkoxycarbonylamino, N-($C_{1-6}$) alkyl-N-($C_{2-6}$)alkoxycarbonylamino, $C_{1-6}$ alkylsulphonylamino, arylsulphonylamino, $C_{1-6}$ alkylsulphonylaminomethyl, aminocarbonylamino, $C_{1-6}$ alkylaminocarbonylamino, di($C_{1-6}$) alkylaminocarbonylamino, mono- or diarylaminocarbonylamino, pyrrolidinylcarbonylamino, piperidinylcarbonylamnino, aminocarbonyl, $C_{1-6}$ alkylaminocarbonyl, di($C_{1-6}$)alkylaminocarbonyl, aminosulphonyl, $C_{1-6}$ alkylaminosulphonyl, di($C_{1-6}$) alkylaminosulphonyl, aminosulphonylmethyl, $C_{1-6}$ alkylaminosulphonylmethyl and di($C_{1-6}$) alkylaminosulphonylmethyl.

As used herein, the expression "$C_{1-6}$ alkyl" includes methyl and ethyl groups, and straight-chained or branched propyl, butyl, pentyl and hexyl groups. Particular alkyl groups are methyl, ethyl, n-propyl, isopropyl and tert-butyl. Derived expressions such as "$C_{1-6}$ alkoxy", "$C_{1-6}$ alkylthio" and "$C_{1-6}$ alkylamino" are to be construed accordingly.

The expression "$C_{2-6}$ alkenyl" as used herein refers to straight-chained and branched alkenyl groups containing from 2 to 6 carbon atoms. Typical examples include vinyl, allyl, dimethylallyl and butenyl groups.

The expression "$C_{2-6}$ alkynyl" as used herein refers to straight-chained and branched alkynyl groups containing from 2 to 6 carbon atoms. Typical examples include ethynyl and propargyl groups.

Typical $C_{3-7}$ cycloalkyl groups include cyclopropyl, cyclobutyl, cyclopentyl and cyclohexyl.

Typical aryl groups include phenyl and naphthyl.

The expression "aryl($C_{1-6}$)alkyl" as used herein includes benzyl, phenylethyl, phenylpropyl and naphthylmethyl.

Suitable heterocycloalkyl groups include azetidinyl, pyrrolidinyl, piperidinyl, piperazinyl and morpholinyl groups.

Suitable heteroaryl groups include pyridinyl, quinolinyl, isoquinolinyl, pyridazinyl, pyrimidinyl, pyrazinyl, pyranyl, flryl, benzofuryl, dibenzofuryl, thienyl, benzthienyl, pyrrolyl, indolyl, pyrazolyl, indazolyl, oxazolyl, isoxazolyl, thiazolyl, isothiazolyl, imidazolyl, benzimidazolyl, oxadiazolyl, thiadiazolyl, triazolyl and tetrazolyl groups.

The expression "heteroaryl($C_{1-6}$)alkyl" as used herein includes furylmethyl, furylethyl, thienylmethyl, thienylethyl, oxazolylmethyl, oxazolylethyl, thiazolylmethyl, thiazolylethyl, imidazolylmethyl, imidazolylethyl, oxadiazolylmethyl, oxadiazolylethyl, thiadiazolylmethyl, thiadiazolylethyl, triazolylmethyl, triazolylethyl, tetrazolylmethyl, tetrazolylethyl, pyridinylmethyl, pyridinylethyl, pyrimidinylmethyl, pyrazinylmethyl, quinolinylmethyl and isoquinolinylmethyl.

The term "halogen" as used herein includes fluorine, chlorine, bromine and iodine, especially fluorine.

For use in medicine, the salts of the compounds of formula I will be pharmaceutically acceptable salts. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, fumaric acid, maleic acid, succinic acid, acetic acid, benzoic acid, oxalic acid, citric acid, tartaric acid, carbonic acid or phosphoric acid. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts.

The present invention includes within its scope prodrugs of the compounds of formula I above. In general, such prodrugs will be functional derivatives of the compounds of formula I which are readily convertible in vivo into the required compound of formula I. Conventional procedures for the selection and preparation of suitable prodrug derivatives are described, for example, in *Design of Prodrugs*, ed. H. Bundgaard, Elsevier, 1985.

Where the compounds according to the invention have at least one asymmetric centre, they may accordingly exist as enantiomers. Where the compounds according to the invention possess two or more asymmetric centres, they may additionally exist as diastereoisomers. For example, the compounds of formula I above wherein Z represents a group of formula (b) or (c) have a chiral centre denoted by the asterisk *, which may accordingly be in the (R) or (S) configuration. It is to be understood that all such isomers and mixtures thereof in any proportion are encompassed within the scope of the present invention.

In particular, the ring junction between the fused five-membered rings in the 2,7-diazabicyclo[3.3.0]octane moiety depicted in formula I is preferably in the cis configuration.

Where E and Q, which may be the same or different, represent straight or branched alkylene chains, these may be, for example, methylene, ethylene, 1-methylethylene, propylene, 2-methylpropylene or butylene. In addition, the alkylene chain Q may be substituted in any position by a hydroxy group giving rise, for example, to a 2-hydroxypropylene or 2-hydroxymethyl-propylene chain Q. Moreover, E may represent a chemical bond such that the moiety Z is attached directly to the central fused bicyclic heteroaromatic ring system containing the variables T, U and V.

Suitably, E represents a chemical bond or a methylene linkage.

Representative alkylene chains for Q include ethylene, propylene, butylene, 2-hydroxypropylene and 2-hydroxymethyl-propylene, especially ethylene.

The compound of formula I in accordance with the present invention is suitably an indole, benzofuran or benzthiophene derivative of formula IA, an indazole derivative of formula IB, or a pyrrolo[2,3-c]-pyridine derivative of formula IC:

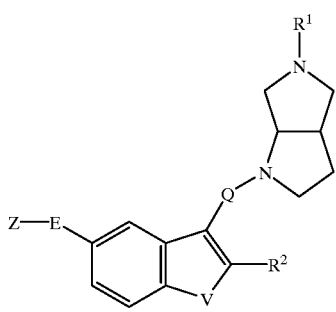
(IA)

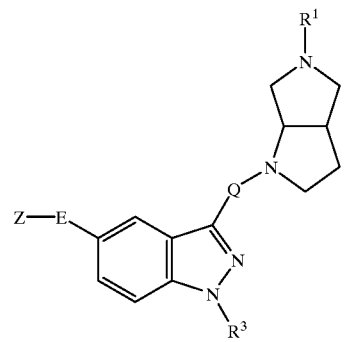
(IB)

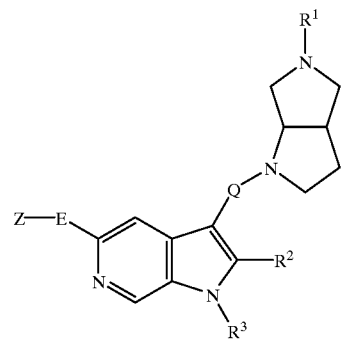
(IC)

wherein Z, E, Q, V, $R^1$, $R^2$ and $R^3$ are as defined above. Preferably, the compounds according to the invention are indole or pyrrolo[2,3-c]pyridine derivatives of formula ID:

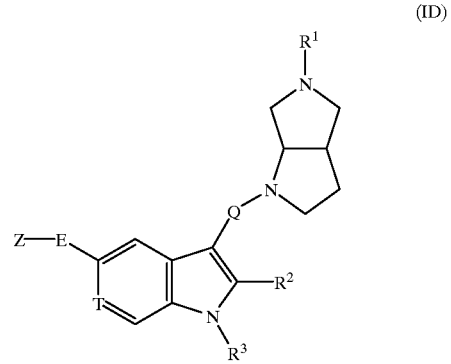
(ID)

wherein Z, E, Q, T, $R^1$, $R^2$ and $R^3$ are as defined above, in particular wherein $R^2$ and $R^3$ are both hydrogen.

Suitable values for the substituent $R^1$ include allyl, dimethylallyl, butenyl, propargyl, benzyl, phenylethyl, furylmethyl, thienylmethyl, imidazolylmethyl and pyridinylmethyl, any of which groups may be optionally substituted by one or more substituents selected typically from halogen, cyano, triazolyl, tetrazolyl, $C_{1-6}$ alkyltetrazolyl, $C_{1-6}$ alkoxy, amino, di($C_{1-6}$)alkylamino, di($C_{1-6}$) alkylaminomethyl, $C_{2-6}$ alkylcarbonylamino, $C_{2-6}$ alkoxycarbonylamino, N-($C_{1-6}$)alkyl-N-($C_{2-6}$) alkoxycarbonylamino, $C_{1-6}$ alkylsulphonylamino, aminocarbonylamino, aminocarbonyl, $C_{1-6}$ alkylaminocarbonyl, di($C_{1-6}$)alkylaminocarbonyl, aminosulphonyl and $C_{1-6}$ alkylaminosulphonylmethyl.

Representative values of $R^1$ include allyl, dimethylallyl, butenyl, propargyl, benzyl, fluorobenzyl, difluorobenzyl, cyanobenzyl, tetrazolyl-benzyl, methyltetrazolyl-benzyl, methoxybenzyl, aminobenzyl, dimethylaminomethyl-benzyl, acetylamino-benzyl, aminocarbonyl-benzyl methylaminocarbonyl-benzyl, dimethylaminocarbonyl-benzyl, aminosulphonyl-benzyl, phenylethyl, fluoro-phenylethyl, difluoro-phenylethyl, cyano-phenylethyl, triazolyl-phenylethyl, amino-phenylethyl, dimethylamino-phenylethyl, acetllamino-phenylethyl, methoxycarbonylamino-phenylethyl, (N-methyl-N-methoxycarbonyl)amino-phenylethyl, aminocarbonylamino-phenylethyl, furylmethyl, thienylmethyl, imidazolylmethyl, pyridinylmethyl and amino-pyridinylmethyl.

Particular values of $R^1$ include benzyl, fluorobenzyl, difluorobenzyl, phenylethyl and furylmethyl.

Suitably, $R^2$ and $R^3$ independently represent hydrogen or methyl, especially hydrogen.

Suitably, $R^4$ represents hydrogen or methyl, especially hydrogen.

Suitably, $R^5$ and $R^6$ are independently selected from hydrogen, methyl, ethyl, n-propyl, isopropyl, n-butyl, tert-butyl, trifluoromethyl, phenyl, methylphenyl (especially 4-methylphenyl), benzyl and phenethyl.

Suitably, the substituent Z represents hydrogen, fluoro, cyano, hydroxy, methoxy, ethoxy, benzyloxy, methylamino-carbonyloxy, cyano-methoxy, aminocarbonyl-methoxy, methylsulphonyl, aminosulphonyl, N-methylamino-sulphonyl, N,N-dimethylamino-sulphonyl, amino, formylamino, acetylamino, trifluoromethyl-carbonylamino, benzyloxy-carbonylamino, methyl-sulphonylamino, ethyl-sulphonylamino, methylphenyl-sulphonylamino, N-methyl-(N-methylsulphonyl)-amino, N-methyl-(N-ethylsulphonyl)-amino, N-methyl-(N-trifluoromethylsulphonyl)-amino, N-ethyl-(N-methylsulphonyl)-amino, N-benzyl-(N-methylsulphonyl)-amino, N-benzyl-(N-ethylsulphonyl)-amino, acetyl, methoxycarbonyl, ethoxycarbonyl, aminocarbonyl, methylaminocarbonyl, ethylaminocarbonyl, propylaminocarbonyl, butylaminocarbonyl, benzylami-nocarbonyl or phenethyl-aminocarbonyl; or a group of formula (a), (b), (c) or (d) as defined above: or an optionally substituted five-membered heteroaromatic rink as specified above.

In a particular embodiment, Z represents $-SO_2NR^5R^6$ in which $R^5$ and $R^6$ are as defined above. In a subset of this embodiment. $R^5$ and $R^6$ independently represent hydrogen or $C_{1-6}$ alkyl, especially hydrogen or methyl. Particular values of Z in this context include aminosulphonyl, N-methylamino-sulphonyl and N,N-dimethylamino-sulphonyl, especially N-methylamino-sulphonyl.

In another embodiment, Z represents a group of formula (b) in which $R^4$ is hydrogen or methyl. In a subset of this embodiment, X and Y both represent oxygen. In a particular aspect of this subset, the chiral centre denoted by the asterisk * is in the (S) configuration.

When the group Z represents an optionally substituted five-membered heteroaromatic ring, this is suitably a 1,3-oxazole, 1,3-thiazole, imidazole, 1,2,4-oxadiazole, 1,3,4-oxadiazole, 1,2,4-thiadiazole, 1,3,4-thiadiazole, 1,2,3-triazole, 1,2,4-triazole or tetrazole ring. Preferably, the ring is a 1,3-oxazole, 1,3-thiazole, 1,2,4-oxadiazole, 1,2,4-thiadiazole or 1,2,4-triazole ring, in particular a 1,2,4-triazol-1-yl or 1,2,4-triazol-4-yl moiety.

Suitably, the five-membered heteroaromatic ring Z is unsubstituted. Examples of optional substituents which may typically be attached to the moiety Z include methyl, ethyl, benzyl and amino.

A particular sub-class of compounds according to the invention is represented by the compounds of formula IIA, and salts and prodrugs thereof:

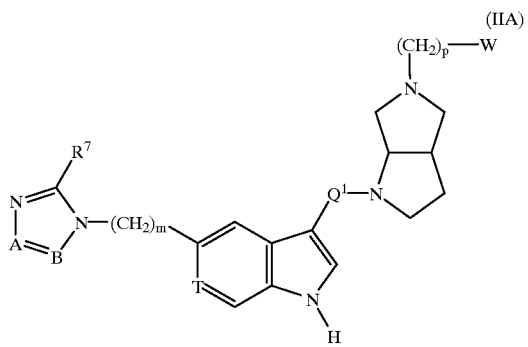

m is zero, 1, 2 or 3;

p is 1, 2 or 3;

$Q^1$ represents a straight or branched alkylene chain containing from 2 to 5 carbon atoms, optionally substituted in any position by a hydroxy group;

T represents nitrogen or CH;

A represents nitrogen or CH;

B represents nitrogen or $C-R^8$;

$R^7$ and $R^8$ independently represent hydrogen, $C_{1-6}$ alkyl, $C_{2-6}$ alkenyl, $C_{3-7}$ cycloalkyl, aryl, aryl($C_{1-6}$)alkyl, $C_{3-7}$ heterocycloalkyl, heteroaryl, heteroaryl($C_{1-6}$)alkyl, $C_{1-6}$ alkoxy, $C_{1-6}$ alkylthio, ammo, $C_{1-6}$ alkylamino, di($C_{1-6}$)alkylamino, halogen, cyano or trifluoromethyl; and W represents a group of formula (Wa), (Wb) or (Wc):

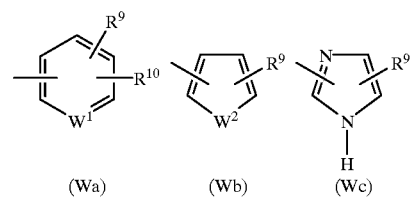

in which $W^1$ represents CH or nitrogen;

$W^2$ represents oxygen, sulphur, NH or N-methyl;

$R^9$ represents hydrogen, halogen, cyano, trifluoromethyl, triazolyl, tetrazolyl, $C_{1-6}$ alkyl-tetrazolyl, $C_{1-6}$ alkoxy, $C_{2-6}$ alkylcarbonyl, amino, $C_{1-6}$ alkylamino, di($C_{1-6}$)alkylamino, di($C_{1-6}$) alkylaminomethyl, $C_{2-6}$ alkylcarbonylamino, $C_{1-6}$ alkylsulphonylamino, aminocarbonylamino, $C_{1-6}$ alkylaminocarbonyl, aminosulphonyl or $C_{1-6}$ alky-laminosulphonylmethyl; and $R^{10}$ represents hydrogen or halogen.

Suitably, $Q^1$ represents a straight or branched 2, 3 or 4 carbon alkylene chain, optionally substituted in any position by a hydroxy group. Particular alkylene chains for $Q^1$ include ethylene, propylene, butylene, 2-hydroxypropylene and 2-(hydroxymethyl)-propylene, especially ethylene.

Particular values of $R^7$ and $R^8$ include hydrogen, methyl, ethyl, benzyl and amino, especially hydrogen.

Particular values of $R^9$ include hydrogen, fluoro, cyano, triazolyl, tetrazolyl, methyl-tetrazolyl, methoxy, amino, dimethylaminomethyl, acetylamino, aminocarbonylamino, methylaminocarbonyl and aminosulphonyl, especially hydrogen or fluoro.

Suitably, $R^{10}$ represents hydrogen or fluoro.

Another sub-class of compounds according to the invention is represented by the compounds of formula IIB, and salts and prodrugs thereof:

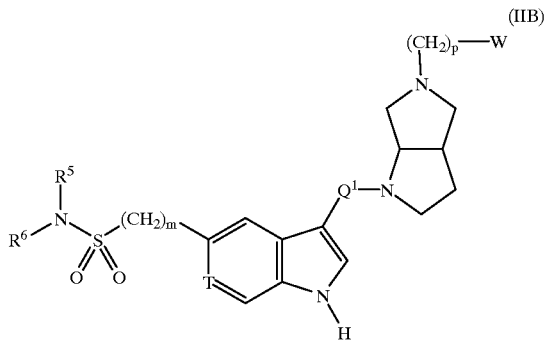

wherein
m, p, $Q^1$, T and W are as defined with reference to formula IIA above; and
$R^5$ and $R^6$ are as defined with reference to formula I above.

Particular values of $R^5$ and $R^6$ in relation to formula IIB above include hydrogen and $C_{1-6}$ alkyl, especially hydrogen or methyl. Suitably, one of $R^5$ and $R^6$ represents hydrogen and the other represents hydrogen or methyl.

A further sub-class of compounds according to the invention is represented by the compounds of formula IIC, and salts and prodrugs thereof:

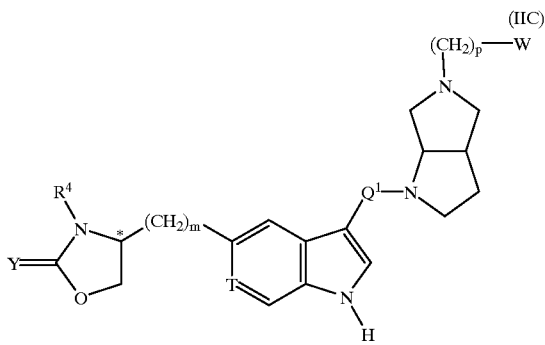

wherein the asterisk * denotes a chiral centre;
m, p, $Q^1$, T and W are as defined with reference to formula IIA above; and
$R^4$ and Y are as defined with reference to formula I above.

Particular values of $R^4$ in relation to formula IIC include hydrogen and methyl, especially hydrogen.

Preferably, Y in formula IIC is oxygen.

Preferably, the chiral centre denoted by the asterisk * in formula IIC is in the (S) configuration.

Specific compounds within the scope of the present invention include:
7-benzyl-2-[2-(5-(1,2,4-triazol-4-yl)-1H-indol-3-yl)ethyl]-cis-2,7-diazabicyclo[3.3.0]octane;
7-(3-furylmethyl)-2-[2-(5-(1,2,4-triazol-4-yl)-1H-indol-3-yl)ethyl]-cis-2,7-diazabicyclo[3.3.0]octane;
7-(2-phenylethyl)-2-[2-(5-(1,2,4-triazol-4-yl)-1H-indol-3-yl)ethyl]-cis-2,7-diazabicyclo[3.3.0]octane;
7-(4-fluorobenzyl)-2-[2-(5-(1,2,4-triazol-4-yl)-1H-indol-3-yl)ethyl]-cis-2,7-diazabicyclo[3.3.0]octane;
7-(2,4-difluorobenzyl)-2-[2-(5-(1,2,4-triazol-4-yl)-1H-indol-3-yl)ethyl]-cis-2,7-diazabicyclo[3.3.0]octane;
and salts and prodrugs thereof.

The invention also provides pharmaceutical compositions comprising one or more compounds of this invention in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. Typical unit dosage forms contain from 1 to 100 mg, for example 1, 2, 5, 10, 25, 50 or 100 mg, of the active ingredient. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

In the treatment of migraine, a suitable dosage level is about 0.01 to 250 mg/kg per day, preferably about 0.05 to 100 mg/kg per day, and especially about 0.05 to 5 mg/kg per day. The compounds may be administered on a regimen of 1 to 4 times per day.

The compounds according to the invention may be prepared by a process which comprises attachment of the $R^1$ moiety to a compound of formula III:

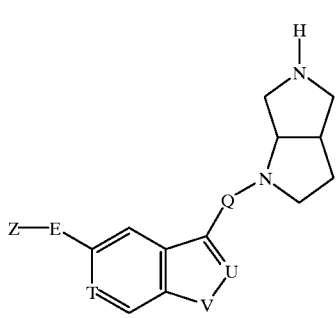

(III)

wherein Z, E, Q, T, U and V are as defined above; by conventional means including N-alkylation.

Attachment of the $R^1$ moiety to the compounds of formula III may conveniently be effected by standard alkylation techniques. One example thereof comprises treatment with an alkenyl halide such as 4-bromobut-1-ene, 4-bromo-2-methylbut-2-ene or allyl bromide, an alkynyl halide such as propargyl bromide, or an aryl($C_{1-6}$)alkyl or heteroaryl($C_{1-6}$)alkyl halide such as 2-bromo-1-[4-(acetylamino)phenyl]-ethane, typically in the presence of sodium carbonate and sodium iodide, in a suitable solvent such as 1,2-dimethoxyethane.

Alternatively, the $R^1$ moiety may conveniently be attached by reductive alkylation, which may be accomplished in a single step, or as a two-step procedure. The single-step approach suitably comprises treating the required compound of formula III as defined above with the appropriate aldehyde, e.g. benzaldehyde, 3-furaldehyde, phenylacetaldehyde, 4-fluorobenzaldehyde, 2,4-difluorobenzaldehyde, pyridine carboxaldehyde, furfuraldehyde or thiophene carboxaldehyde, in the presence of a reducing agent such as sodium cyanoborohydride. In a typical two-step procedure, for the preparation of a compound of formula I wherein $R^1$ corresponds to a group of formula —$CH_2R^{11}$, a carboxylic acid derivative of formula $R^{11}$—$CO_2H$ is condensed with the required compound of formula III, suitably in the presence of 1-(3-dimethylaminopropyl)-3-ethylcarbodiimide hydrochloride and 1-hydroxybenzotriazole hydrate, to afford a compound corresponding to formula I wherein $R^1$ represents —$COR^{11}$; the carbonyl group thereof can then be reduced, for example by treatment with diisobutylaluminium hydride, and the required compound of formula I thereby obtained.

The compounds of formula III above wherein T represents CH, U represents C—$R^2$ and V represents N—$R^3$, corresponding to the indole derivatives of formula ID as defined above wherein T represents CH and $R^1$ is hydrogen, may be prepared by a process which comprises reacting a compound of formula IV:

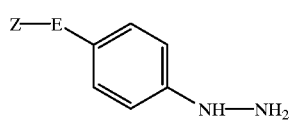

(IV)

wherein Z and E are as defined above; with a compound of formula V, or a carbonyl-protected form thereof:

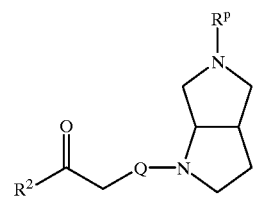

(V)

wherein $R^2$ and Q are as defined above, and $R^P$ represents an amino-protecting group; followed, where required, by N-alkylation by standard methods to introduce the moiety $R^3$; with subsequent removal of the amino-protecting group $R^P$.

The reaction between compounds IV and V, which is an example of the well-known Fischer indole synthesis, is suitably carried out by heating the reagents together under mildly acidic conditions, e.g. 4% sulphuric acid at reflux.

Suitable carbonyl-protected forms of the compounds of formula V include the dimethyl acetal or ketal derivatives.

The protecting group $R^P$ in the compounds of formula V is suitably a carbamoyl moiety such as tert-butoxycarbonyl (BOC), which can conveniently be removed as necessary by treatment under mildly acidic conditions. Indeed, the acidic conditions of the Fischer indole synthesis reaction will generally suffice to remove the BOC group. An alternative protecting group $R^P$ is methoxycarbonyl, which can conveniently be removed as necessary by treatment with hydrazine hydrate and potassium hydroxide in the presence of ethylene glycol at an elevated temperature.

The Fischer reaction between compounds IV and V may be carried out in a single step, or may proceed via an initial non-cyclising step at a lower temperature to give an intermediate of formula VI:

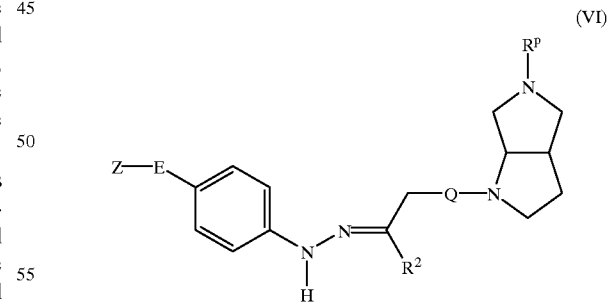

(VI)

wherein Z, E, Q, $R^2$ and $R^P$ are as defined above; followed by cyclisation using a suitable reagent, e.g. a polyphosphate ester.

The intermediates of formula V, or carbonyl-protected forms thereof, may be prepared by reacting a compound of formula VII, or a carbonyl-protected form thereof, with a compound of formula VIII:

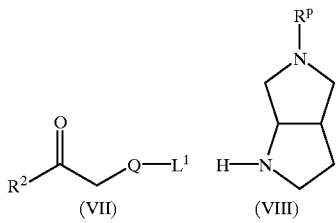

(VII)                (VIII)

wherein Q, $R^2$ and $R^p$ are as defined above, and $L^1$ represents a suitable leaving group.

The leaving group $L^1$ is suitably a halogen atom, e.g. chlorine or bromine.

Where $L^1$ represents a halogen atom, the reaction between compounds VII and VIII is conveniently effected by stirring the reactants under basic conditions in a suitable solvent, for example sodium carbonate in 1,2-dimethoxyethane, typically in the presence of catalytic sodium iodide.

The compounds according to the invention wherein T represents CH, U represents C—$R^2$ and V represents N—$R^3$—i.e. the indole derivatives of formula ID as defined above wherein T represents CH—may alternatively be prepared by a process which comprises reacting a compound of formula IV as defined above with a compound of formula IX, or a carbonyl-protected form thereof:

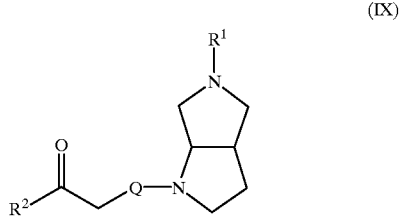
(IX)

wherein Q, $R^1$ and $R^2$ are as defined above; under conditions analogous to those described above for the reaction between compounds IV and V; followed, where required, by N-alkylation by standard methods to introduce the moiety $R^3$.

As for the compounds of formula V, suitable carbonyl-protected forms of the compounds of formula IX include the dimethyl acetal or ketal derivatives. Where the alkylene chain Q is substituted by a hydroxy group, this group may condense with the carbonyl moiety in compounds V and IX, whereby the carbonyl moiety is protected in the form of a cyclic hemiacetal.

As with that between compounds IV and V, the Fischer reaction between compounds IV and IX may be carried out in a single step, or may proceed via an initial non-cyclising step at a lower temperature to give an intermediate of formula X:

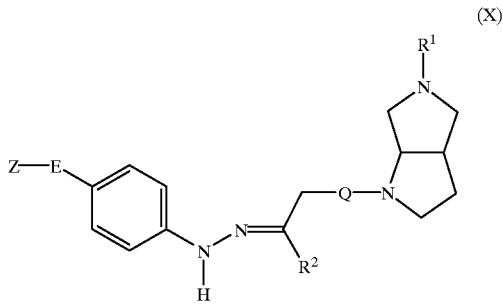
(X)

wherein Z, E, Q, $R^1$ and $R^2$ are as defined above; followed by cyclisation using a suitable reagent, e.g. a polyphosphate ester.

The intermediates of formula IX, or carbonyl-protected forms thereof, may be prepared by reacting a compound of formula VII as defined above, or a carbonyl-protected form thereof, with a compound of formula XI:

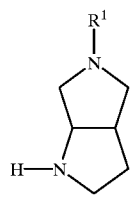
(XI)

wherein $R^1$ is as defined above; under conditions analogous to those described above for the reaction between compounds VII and VIII.

In an alternative procedure, the compounds of formula III above may be prepared by a process which comprises reacting a compound of formula VIII as defined above with a compound of formula XII:

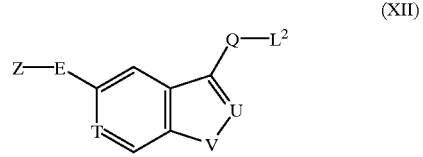
(XII)

wherein Z, E, Q, T, U and V are as defined above, and $L^2$ represents a suitable leaving group; followed by removal of the amino-protecting group $R^p$.

Similarly, the compounds of formula I as defined above may be prepared by a process which comprises reacting a compound of formula XI as defined above with a compound of formula XII as defined above.

The leaving group $L^2$ is suitably an alkylsulphonyloxy or arylsulphonyloxy group, e.g. methanesulphonyloxy (mesyloxy) or p-toluenesulphonyloxy (tosyloxy).

Where $L^2$ represents an alkylsulphonyloxy or arylsulphonyloxy group, the reaction between compound XII and compound VIII or XI is conveniently carried out in a suitable solvent such as t,1,2-dimethoxsethane or isopropyl alcohol, optionally in the presence of a cosolvent such as acetonitrile, typically in the presence of a base such as sodium carbonate or potassium carbonate, and optionally with the addition of sodium iodide.

In a representative embodiment, the compounds of formula XII wherein T and U both represent CH, V represents NH, Q represents a propylene chain and $L^2$ represents a mesyloxy or tosyloxy group may be prepared by reacting 3,4-dihydro-2H-pyran with a compound of formula IV as defined above or a salt thereof, under a variant of the Fischer reaction conditions as described above for the reaction between compounds IV and V; followed by mesylation or tosylation of the 3-hydroxypropyl-indole derivative thereby obtained, typically by treatment with mesyl chloride or tosyl chloride under standard conditions.

The Fischer reaction with 3,4-dihydro-2H-pyran is suitably brought about by heating the hydrazine derivative IV or an acid addition salt thereof, typically the hydrochloride salt, in an inert solvent such as dioxan, advantageously in the presence of a mineral acid such as hydrochloric acid or a Lewis acid such as zinc chloride, at the reflux temperature of the solvent.

In a further procedure, the compounds of formula III above wherein T represents CH, U represents nitrogen and V represents N—$R^3$, corresponding to the indazole derivatives of formula IB as defined above wherein $R^1$ is hydrogen, may be prepared by a process which comprises cyclising a compound of formula XIII:

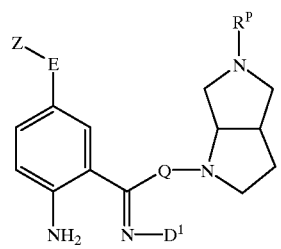

(XIII)

wherein Z, E, Q and $R^P$ are as defined above, and $D^1$ represents a readily displaceable group; followed, where required, by N-alkylation by standard methods to introduce the moiety $R^3$; with subsequent removal of the amino-protecting group $R^P$.

Similarly, the compounds of formula I wherein T represents CH, U represents nitrogen and V represents N—$R^3$— i.e. the indazole derivatives of formula IB as defined above—may be prepared by a process which comprises cyclising a compound of formula XIV:

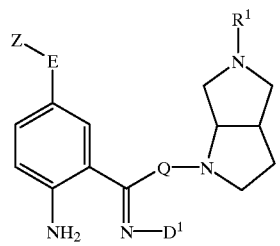

(XIV)

in which Z, E, Q, $R^1$ and $D^1$ are as defined above; followed, where required, by N-alkylation by standard methods to introduce the moiety $R^3$.

The cyclisation of compounds XIII and XIV is conveniently achieved in a suitable organic solvent at an elevated temperature, for example in a mixture of m-xylene and 2,6-lutidine at a temperature in the region of 140° C.

The readily displaceable group $D^1$ in the compounds of formula XIII and XIV suitably represents a $C_{1-4}$ alkanoyloxy group, preferably acetoxy. Where $D^1$ represents acetoxy, the desired compound of formula XIII or XIV may be conveniently prepared by treating a carbonyl compound of formula XV:

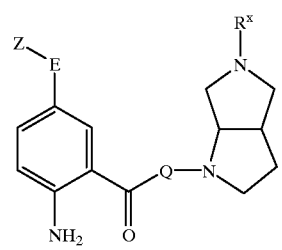

(XV)

wherein Z, E and Q are as defined above, and $R^x$ corresponds to the group $R^1$ as defined above, or $R^x$ represents an amino-protecting group as defined for $R^P$; or a protected derivative thereof, preferably the N-formyl protected 4-dimethylaminopyridine, in dichloromethane at room temperature.

The N-formyl protected derivatives of the intermediates of formula XV may conveniently be prepared by ozonolysis of the corresponding indole derivative of formula XVI:

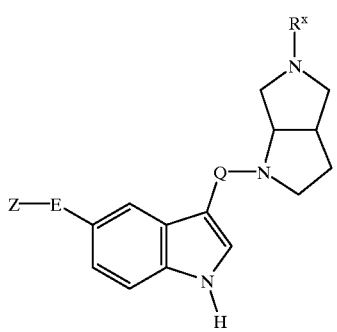

(XVI)

wherein Z, E, Q and $R^x$ are as defined above; followed by a reductive workup, advantageously using dimethylsulphide.

The indole derivatives of formula XVI may be prepared by methods analogous to those described in the accompanying Examples, or by procedures well known from the art.

In a still further procedure, the compounds of formula III above wherein T represents CH, U represents C—$R^2$ and V represents oxygen or sulphur, corresponding to the benzofuran or benzthiophene derivatives of formula IA wherein V is oxygen or sulphur respectively and $R^1$ is hydrogen, may be prepared by a process which comprises cyclising a compound of formula XVII:

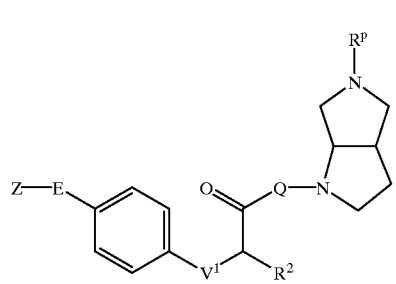

(XVII)

wherein Z, E, Q, $R^2$ and $R^P$ are as defined above, and $V^1$ represents oxygen or sulphur; followed by removal of the amino-protecting group $R^P$.

Similarly, the compounds of formula I wherein T represents CH, U represents C—R² and V represents oxygen or sulphur—i.e. the benzofuran or benzthiophene derivatives of formula IA above—may be prepared by a process which comprises cyclising a compound of formula XVIII:

(XVIII)

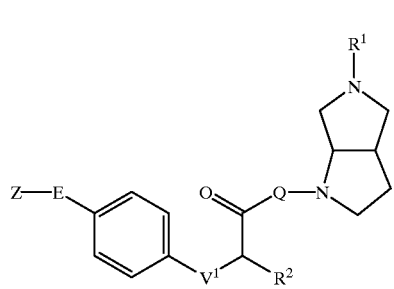

wherein Z, E, Q, R¹, R² and V¹ are as defined above.

The cyclisation of compounds XVII and XVIII is conveniently effected by using polyphosphoric acid or a polyphosphate ester, advantageously at an elevated temperature.

The compounds of formula XVII and XVIII may be prepared by reacting a compound of formula XIX with a compound of formula XX:

(XIX)

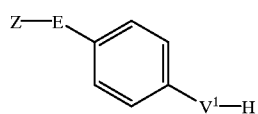

(XX)

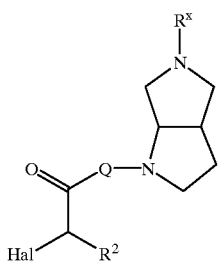

wherein Z, E, Q, R², V¹ and R$^x$ are as defined above, and Hal represents a halogen atom.

The reaction is conveniently effected in the presence of a base such as sodium hydroxide.

The hydroxy and mercapto derivatives of formula XIX may be prepared by a variety of methods which will be readily apparent to those skilled in the art. One such method is described in EP-A-0497512.

In a yet further procedure, the compounds of formula III above may be prepared by a process which comprises reducing a compound of formula XXI:

(XXI)

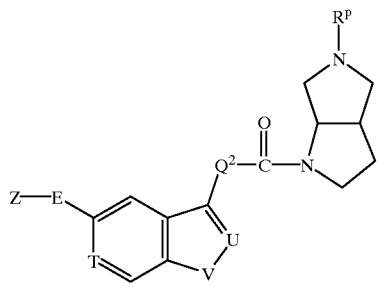

wherein Z, E, T, U, V and R$^p$ are as defined above, and —Q²—CH₂— corresponds to the moiety Q as defined above; with subsequent removal of the amino-protecting group R$^p$.

Similarly, the compounds according to the invention may be prepared by a process which comprises reducing a compound of formula XXII:

(XXII)

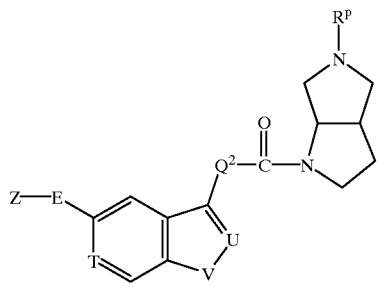

wherein Z, E, T, U, V, R¹ and Q² are as defined above.

The reduction of compounds XXI and XXII is conveniently effected by treating the appropriate compound with a reducing agent such as lithium aluminium hydride in an appropriate solvent, e.g. diethyl ether or tetrahydrofuran, or mixtures thereof.

The compounds of formulae XXI and XXII above may suitably be prepared by reacting a compound of formula XXIII with the appropriate compound of formula XXIV:

(XXIII)

(XXIV)

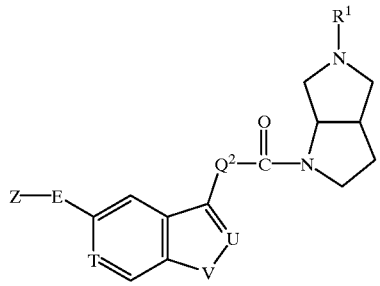

wherein Z, E, T, U, V, R$^x$ and Q² are as defined above, and J represents a reactive carboxylate moiety.

Suitable values for the reactive carboxylate moiety J include esters, for example $C_{1-4}$ alkyl esters; acid anhydrides, for example mixed anhydrides with $C_{1-4}$ alkanoic acids; acid halides, for example acid chlorides; and acylimidazoles.

By way of example, the intermediates of formula XXIII above wherein J is an acid chloride moiety may be prepared by treating the corresponding carboxylic acid derivative with thionyl chloride in toluene. Similarly, the intermediates of formula XXIII wherein J is an acylimidazole moiety may be prepared by treating the corresponding carboxylic acid derivative with 1,1'-carbonyldiimidazole. Alternatively, the reactive carboxylate moiety J may be obtained by treating the corresponding compound wherein J is carboxy with 1-(3-dimethylaminopropyl)-3-ethylcarbodiimide hydrochloride and 1-hydroxybenzotriazole hydrate, optionally in the presence of triethylamine; the resulting activated carboxylate intermediate may then suitably be reacted in situ with the required compound of formula XXIV.

The hydrazine derivatives of formula IV above may be prepared by methods analogous to those described in EP-A-0438230, EP-A-0497512, EP-A-0548813 and WO-A-91/18897.

The 2,7-diazabicyclo[3.3.0]octane intermediates of formulae VIII, XI and XXIV above may be prepared by the procedures described in EP-A-0393424, or by methods analogous thereto.

Where they are not commercially available, the starting materials of formula VII, XX and XXIII may be prepared by methods analogous to those described in the accompanying Examples, or by standard procedures well known from the art.

It will be understood that any compound of formula I initially obtained from any of the above processes may, where appropriate, subsequently be elaborated into a further compound of formula I by techniques known from the art. For example, a compound of formula I wherein $R^1$ is benzyl initially obtained may be converted by catalytic hydrogenation to the corresponding compound of formula III, which in turn may be converted into a further compound of formula I using standard N-alkylation techniques as described above. Furthermore, a compound of formula I initially obtained wherein the $R^1$ moiety is substituted by nitro or cyano may be converted by catalytic hydrogenation to the corresponding amino- or aminomethyl-substituted compound respectively. Additionally, a compound of formula I wherein the $R^1$ moiety is substituted by hydroxy, possibly obtained by lithium aluminium hydride reduction of a precursor alkoxycarbonyl derivative, may be mesylated under standard conditions, and the mesyl group subsequently displaced by an amino moiety by treatment with the desired amine in a sealed tube at an elevated temperature. The amine derivative resulting from any of these procedures may then, for example, be N-acylated using the appropriate acyl halide, e.g. acetyl chloride; or aminocarbonylated, using potassium isocyanate, to the corresponding urea derivative; or converted to a 1,2,4-triazol-4-yl derivative using N,N-dimethylformamide azine; or reductively alkylated by treatment with the appropriate aldehyde or ketone in the presence of sodium cyanoborohydride. If desired, the amine derivative may also be carbamoylated by treatment with the requisite alkyl chloroformate. A compound of formula I initially obtained wherein the $R^1$ moiety is substituted by cyano may be converted, by treatment with sodium azide, to the corresponding tetrazole derivative, which in turn may be alkylated on the tetrazole ring by treatment with an alkyl halide under standard conditions. By way of additional illustration, a compound of formula I initially obtained wherein the $R^1$ moiety is substituted by an alkoxycarbonyl moiety may be saponified, by treatment with an alkali metal hydroxide, to the corresponding carboxy-substituted compound, which in turn may be converted to an amide derivative by treatment with the appropriate amine, advantageously in the presence of 1-(3-dimethylaminopropyl)-3-ethylcarbodiimide hydrochloride and 1-hydroxybenzotriazole. Moreover, a compound of formula I wherein $R^3$ is hydrogen initially obtained may be converted into a compound of formula I wherein $R^3$ represents $C_{1-6}$ alkyl by standard alkylation techniques, for example by treatment with an alkyl iodide, e.g. methyl iodide, typically under basic conditions, e.g. sodium hydride in dimethylformamide, or triethylamine in acetonitrile.

Where the above-described processes for the preparation of the compounds according to the invention give rise to mixtures of stereoisomers, these isomers may be separated by conventional techniques such as preparative chromatography. The novel compounds may be prepared in racemic form, or individual enantiomers may be prepared either by enantiospecific synthesis or by resolution. The novel compounds may, for example, be resolved into their component enantiomers by standard techniques such as preparative HPLC, or the formation of diastereomeric pairs by salt formation with an optically active acid, such as (−)-di-p-toluoyl-d-tartaric acid and/or (+)-di-p-toluoyl-l-tartaric acid, followed by fractional crystallization and regeneration of the free base. The novel compounds may also be resolved by formation of diastereomeric esters or amides, followed by chromatographic separation and removal of the chiral auxiliary.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

The following Examples illustrate the preparation of compounds according to the invention.

The compounds in accordance with the present invention potently and selectively bind to the 5-$HT_{1D\alpha}$ receptor subtype, inhibit forskolin-stimulated adenylyl cyclase activity, and stimulate [$^{35}$S]-GTP$_\gamma$S binding to membranes from clonal cell lines expressing human cloned receptors.

5-$HT_{1D\alpha}$/5-$HT_{1D\beta}$ Radioligand Binding

Chinese hamster ovary (CHO) clonal cell lines expressing the human 5-$HT_{1D\alpha}$ and 5-$HT_{1D\beta}$ receptors were harvested in PBS and homogenised in ice cold 50 mM Tris-HCl (pH 7.7 at room temperature) with a Kinematica polytron and centrifuged at 48,000 g at 4° C. for 11 min. The pellet was then resuspended in 50 mM Tris-HCl followed by a 10 min incubation at 37° C. Finally the tissue was recentrifuged at 48,000 g, 4° C. for 11 min and the pellet resuspended, in assay buffer (composition in mM: Tris-HCl 50, pargyline 0.01, $CaCl_2$ 4; ascorbate 0.1%; pH 7.7 at room temperature) to give the required volume immediately prior to use (0.2 mg protein/ml). Incubations were carried out for 30 min at 37° C. in the presence of 0.02–150 nM [$^3$H]-5-HT for saturation studies or 2–5 nM [$^3$H]-5-HT for displacement studies. The final assay volume was 1 ml. 5-HT (10 μM) was used to define non-specific binding. The reaction was initiated by the addition of membrane and was terminated by rapid filtration through Whatman GF/B filters (presoaked in 0.3% PEI/0.5% Triton X) followed by 2×4 ml washings with 50 mM Tris-HCl. The radioactive filters were then counted on a LKB beta or a Wallac beta plate counter. Binding parameters were determined by non-linear, least squares regression analysis using an iterative curve fitting routine, from which $IC_{50}$ (the molar concentration of compound necessary to inhibit binding by 50%) values could be calculated for each test compound. The $IC_{50}$ values for binding to the 5-$HT_{1D\alpha}$ receptor subtype obtained for the compounds of the accompanying Examples were below 50 nM in each case. Furthermore, the compounds of the accompanying Examples were all found to possess a selective affinity for the 5-$HT_{1D\alpha}$ receptor subtype of at least 10-fold relative to the 5-$HT_{1D\beta}$ subtype.

5-$HT_{1D\alpha}$/5-$HT_{1D\beta}$ Adenylyl Cyclase Assay

Studies were performed essentially as described in *J. Pharmacol. Exp. Ther.*, 1986, 238, 248. CHO clonal cell lines expressing the human cloned 5-$HT_{1D\alpha}$ and 5-$HT_{1D\beta}$ receptors were harvested in PBS and homogenised, using a motor driven teflon/glass homogeniser, in ice cold Tris HCl-EGTA buffer (composition in mM: Tris HCl 10, EGTA 1, pH 8.0 at room temperature) and incubated on ice for 30–60 min. The tissue was then centrifuged at 20,000 g for 20 min at 4° C., the supernatant discarded and the pellet resuspended in Tris HCl-EDTA buffer (composition in mM: Tris HCl 50, EDTA 5, pH 7.6 at room temperature) just prior to assay. The adenylyl cyclase activity was determined by measuring the conversion of $\alpha$-[$^{33}$P]-ATP to [$^{33}$P]-cyclic AMP. A 10 $\mu$l aliquot of the membrane suspension was incubated, for 10–15 min, in a final volume of 50 $\mu$l, at 30° C., with or without forskolin (10 $\mu$M), in the presence or absence of test compound. The incubation buffer consisted of 50 mM Tris HCl (pH 7.6 at room temperature), 100 mM NaCl, 30 $\mu$M GTP, 50 $\mu$M cyclic AMP, 1 mM dithiothreitol, 1 mM ATP, 5 mM $MgCl_2$, 1 mM EGTA, 1 mM 3-isobutyl-1-methylxanthine, 3.5 mM creatinine phosphate, 0.2 mg/ml creatine phosphokinase, 0.5–1 $\mu$Ci $\alpha$-[$^{33}$P]-ATP and 1 nCi [$^3$H]-cyclic AMP. The incubation was initiated by the addition of membrane, following a 5 min preincubation at 30° C., and was terminated by the addition of 100 $\mu$l SDS (composition in mM: sodium lauryl sulphate 2%, ATP 45, cyclic AMP 1.3, pH 7.5 at room temperature). The ATP and cyclic AMP were separated on a double column chromatography system (*Anal. Biochem.*, 1974, 58, 541). Functional parameters were determined using a least squares curve fitting programme ALLFIT (*Am. J. Physiol.*, 1978, 235, E97) from which $E_{max}$ (maximal effect) and $EC_{50}$ (the molar concentration of compound necessary to inhibit the maximal effect by 50%) values were obtained for each test compound. Of those compounds which were tested in this assay, the $EC_{50}$ values for the 5-$HT_{1D\alpha}$ receptor obtained for the compounds of the accompanying Examples were below 500 nM in each case. Moreover, the compounds of the accompanying Examples which were tested were all found to possess at least a 10-fold selectivity for the 5-$HT_{1D\alpha}$ receptor subtype relative to the 5-$HT_{1D\beta}$ subtype.

5-$HT_{1D\alpha}$/5-$HT_{1D\beta}$ GTP$_\gamma$S Binding

Studies were performed essentially as described in *Br. J. Pharmacol.*, 1993, 109, 1120. CHO clonal cell lines expressing the human cloned 5-$HT_{1D\alpha}$ and 5-$HT_{1D\beta}$ receptors were harvested in PBS and homogenised using a Kinematica polytron in ice cold 20 mM HEPES containing 10 mM EDTA, pH 7.4 at room temperature. The membranes were then centrifuged at 40,000 g, 4° C. for 15 min. The pellet was then resuspended in ice cold 20 mM HEPES containing 0.1 mM EDTA, pH 7.4 at room temperature and recentrifuged at 40,000 g, 4° C. for 15–25 minutes. The membranes were then resuspended in assay buffer (composition in mM: HEPES 20, NaCl 100, $MgCl_2$ 10, pargyline 0.01; ascorbate 0.1%; pH 7.4 at room temperature) at a concentration of 40 $\mu$g protein/ml for the 5-$HT_{1D\alpha}$ receptor transfected cells and 40–50 $\mu$g protein/ml for the 5-$HT_{1D\beta}$ receptor transfected cells. The membrane suspension was then incubated, in a volume of 1 ml, with GDP (100 $\mu$M for 5-$HT_{1D\alpha}$ receptor transfected cells, 30 $\mu$M for the 5-$HT_{1D\beta}$ receptor transfected cells) and test compound at 30° C. for 20 min and then transferred to ice for a further 15 min. [$^{35}$S]-GTP$_\gamma$S was then added at a final concentration of 100 pM and the samples incubated for 30 min at 30° C. The reaction was initiated by the addition of membrane and was terminated by rapid filtration through Whatman GF/B filters and washed with 5 ml water. The radioactive filters were then counted on a LKB beta counter. Functional parameters were determined by a non-linear, least squares regression analysis using an iterative curve fitting routine, from which $E_{max}$ (maximal effect) and $EC_{50}$ (the molar concentration of compound necessary to inhibit the maximal effect by 50%) values were obtained for each test compound. Of those compounds which were tested in this assay, the $EC_{50}$ values for the 5-$HT_{1D\alpha}$ receptor obtained for the compounds of the accompanying Examples were below 500 nM in each case. Moreover, the compounds of the accompanying Examples which were tested were all found to possess at least a 10-fold selectivity for the 5-$HT_{1D\alpha}$ receptor subtype relative to the 5-$HT_{1D\beta}$ subtype.

EXAMPLE 1 cis-3-(2-(5-Benzyl-hexahydro-pyrrolo[3,4-b]pyrrol-1-yl)-ethyl)-5-[1,2,4]triazol-4-yl-1H indole. 1.75 Hydrozen oxalate. 0.75 Hydrate (enantiomer B)

Intermediate 1: R-(1-Phenyl-ethylamino)-acetic acid methyl ester

R-(+)-alpha-methylbenzylamine (61 lg, 503 mmol) was added to a stirred solution/suspension of methylbromoacetate (77 g, 503 mmol) and anhydrous potassium carbonate (80 g, 755 mmol) in dry dimethylformamide (1 L) at room temperature, under nitrogen. The mixture was stirred and heated to 80° C. for 2 hours. After cooling the potassium carbonate was removed by filtration. The filtrate was then evaporated, and the residue was partitioned between hexane and water. The organic layer was further extracted and washed with water (×2), then dried ($MgSO_4$), filtered and evaporated. The residue was purified by distillation to give the title amino-ester (58 g, 60%) b.p. 90–100° C. @ 1.5 mbar; $\delta$ (360 MHz, $CDCl_3$) 1.38 (3H, d, J=6.6 Hz, CHC$\underline{H}_3$), 3.23 (1H, d, J=17.4 Hz, 1 of NC$\underline{H}_2CO_2$Me), 3.31 (1H, d, 17.4 Hz, 1 of NC$\underline{H}_2CO_2$Me), 3.69 (3H, s, $CO_2C\underline{H}_3$), 3.79 (1H, s, C$\underline{H}$Me), 7.20–7.26 (1H, m, Ar-H), 7.30–7.36 (4H, m, Ar-H).

Intermediate 2: R-(1-Phenyl-ethylamino)-acetic acid

A mixture of R-(1-phenyl-ethylamino) acetic acid methyl ester (12.3 g, 64 mmol) and water (30 ml) was stirred vigorously and heated at reflux for 24 hours. The mixture was allowed to cool, then washed with ethyl acetate. The aqueous was then evaporated (using ethanol to azeotrope to dryness) to yield the title acid (9.5 g, 83%) as a colourless solid; $\delta$ (250 MHz, $d_6$-DMSO+$D_2O$) 1.55 (3H, d, J=6.9 Hz, CHC$\underline{H}_3$), 2.94 (1H, d, J=15.6 Hz, 1 of NC$\underline{H}_2CO_2$Me), 3.11 (1H, d, J=15.6 Hz, 1 of NC$\underline{H}_2CO_2$Me), 4.31 (1H, q, J=6.8 Hz, C$\underline{H}CH_3$), 7.42–7.54 (5H, m, Ar-H).

Intermediate 3: 1-(1-Phenyl-ethyl)-hexahydro-pyrrolo[3,4-b]pyrrole-5-carboxylic acid methyl ester A mixture of allyl-(2-oxo-ethyl)-carbamic acid methyl ester [EP 0 393 424 A2] (8.8 g, 56 mmol) and R-(1phenylethylamino)acetic acid (9.5 g, 53 mmol) in dry toluene (150 ml) was stirred and heated at reflux under nitrogen with azeotropic removal of water for 3 hours. Upon cooling the solvent was removed under vacuum, and the residue was purified by chromatography on silica gel eluting with 50%→60%→80% EtOAc/hexane, then 100% EtOAc to give Diastereomer A (less polar, 5.7 g, 39%, thick oil); δ (360 MHz,CDCl$_3$) 1.37 (3H, d, J=6.7 Hz, CHC$\underline{H}_3$); 1.56–1.63 (1H, m), 1.91–2.00 (1H, m), 2.39–2.45 (1H, m), 2.68–2.76 (1H, m), 2.77–2.83 (1H, m), 3.24–3.68 (6H, m), 3.70 (3H, s, CO$_2$Me), 7.20–7.34 (5H, m, ArH), and Diastereomer B (more polar, 5.0 g, 34%, thick oil); δ (360 MHz, CDCl$_3$) 1.38 (3H, d, J=6.6 Hz, CHC$\underline{H}_3$), 1.55–1.64 (1H, m), 1.98–2.06 (1H, m), 2.46–2.52 (1H, m), 2.66–2.78 (1H, br m), 2.86–3.24 (3H, br m), 3.26–3.46 (3H, br m), 3.52 (1H, q, J=6.6 Hz, C$\underline{H}$CH$_3$), 3.63 (3H, s, CO$_2$Me), 7.22–7.36 (5H, m, Ar-H).

Intermediate 4: cis-Hexahydro-pyrrolo[3,4-b]pyrrole-5-carboxylic acid methyl ester (enantiomer B)

10% Pd/C (1 g) was added to a solution of 1-(1-phenyl-ethyl)-hexahydro-pyrrolo[3,4-b]pyrrole-5-carboxylic acid methyl ester (Diastereomer B, 4.9 g, 17.9 mmol), ammonium formate (5.6 g, 89 mmol) and 5N hydrochloric acid (4.0 ml, 20 mmol) in methanol (180 ml) at room temperature under nitrogen. The mixture was stirred and heated at reflux for 1 hour. Upon cooling the catalyst was removed by filtration through celite (washing with methanol). The filtrate was evaporated and the residue was partitioned between dichloromethane and saturated aqueous potassium carbonate. The aqueous layer was further extracted with dichloromethane (×1) and n-butanol (×1). The combined extracts were evaporated, and the residue was purified by chromatography on silica gel eluting with CH$_2$Cl$_2$/MeOH/NH$_3$ (80:8:1) to give the title amine (2.7 g, 89%) as a pale yellow oil; δ (360 MHz, d$_6$-DMSO) 1.50–1.58 (1H, m), 1.76–1.86 (1H, m), 2.66 (1H, br s), 2.76–2.88 (2H, m), 3.04–3.08 (1H, m), 3.10 (1H, br s, NH), 3.18 (1H, dd, J=11.4, 2.5 Hz), 3.40–3.52 (2H, m), 3.56 (3H, s, CO$_2\underline{Me}$), 3.66 (1H, br s).

Intermediate 5: (cis)-1-(4,4-Dimethoxy-butyl)-hexahydro-pyrrolo[3,4-b]pyrrole-5-carboxylic acid methyl ester (enantiomer B)

A mixture of cis-hexahydro-pyrrolo[3,4-b]pyrrole-5-carboxylic acid methyl ester (enantiomer B, 2.6 g, 15.3 mmol), 4-chlorobutanal-dimethylacetal (2.3 g, 15.1 mmol), sodium iodide (2.5 g, 16.7 mmol) and sodium carbonate (1.8 g, 16.9 mmol) in dry 1,2-dimethoxyethane (45 ml) was stirred and heated at reflux under nitrogen for 16 hours. Upon cooling the volatiles were removed in vacuo and the residue was partitioned between ethyl acetate and saturated aqueous potassium carbonate. The aqueous layer was further extracted with ethyl acetate (×2). The combined extracts were dried (Na$_2$SO$_4$), filtered and evaporated. The residue was purified by chromatography on silica gel, eluting with CH$_2$Cl$_2$/MeOH/NH$_3$ (95:5:0.5) to give the title acetal (4.1 g, 94%) as an orange oil; δ (250 MHz, CDCl$_3$) 1.50–1.60 (5H, m), 1.98–2.08 (1H, m), 2.18–2.36 (2H, m), 2.56–2.80 (2H, m), 2.94 (1H, br s), 3.16–3.62 (1H, m, includes 3.32, 6H, s, (O$\underline{Me}$)$_2$), 3.68 (3H, s, CO$_2$Me), 4.38 (1H, t, J=5.3 Hz, C$\underline{H}$(OMe)$_2$).

Intermediate 6: cis-1 -[2-(5-[1,2,4]Triazol-4-yl-1H-indol-3-yl)-ethyl]-hexahydro-pyrrolo[3,4-b]pyrrrole-5-carboxylic acid methyl ester (enantiomer B)

4'-([1,2,4]Triazol-4-yl)-phenyl hydrazine (EP 581 538) (2.6 g, 14.8 mmol) was added to a stirred solution of cis-1-(4,4-dimethoxy-butyl)-hexahydro-pyrrolo[3,4-b]pyrrole-5-carboxylic acid methyl ester (enantiomer B) (4.1 g, 14.3 mmol) in 4% sulphuric acid (75 ml) at room temperature. After 15 minutes at room temperature the mixture was heated at reflux for 24 hours. The mixture was then cooled to 0° C. and carefully neutralised with potassium carbonate (s). The aqueous was then extracted with n-butanol (×4). The combined extracts were evaporated and the residue was purified by chromatography on silica gel eluting with CH$_2$Cl$_2$/MeOH/NH$_3$ (95:5:0.5→100:8:1) to give the title indole (1.9 g, 35%) as a yellow foam; δ (360 MHz, CDCl$_3$) 1.62–1.76 (1H, m), 2.02–2.16 (1H, m), 2.39 (1H, dd, J=16.9, 9.1 Hz), 2.64–2.68 (1H, m), 2.78 (1H, br s), 2.92–3.08 (4H, m), 3.48–3.62 (2H, m), 3.67 (3H, s, CO$_2$Me), 7.14 (1H, dd, J=8.5, 2.0 Hz, Ar—H), 7.23 (1H, s, Ar—H), 7.48 (1H, d, J=8.6 Hz, Ar—H), 7.55 (1H, d, J=2.1 Hz, Ar—H), 8.46 (1H, br s, NH), 8.48 (2H, s, Triazole-H).

Intermediate 7: cis-1-[2-(5-[1,2,4]Triazol-4-yl-1H-indol-3-yl)-ethyl]-hexahydro-pyrrolo[3,4-b]pyrrole (enantiomer B)

A mixture of cis-1-[2-(5-[1,2,4]triazol-4-yl-1H-indol-3-yl)-ethyl)-hexahydro-pyrrolo[3,4-b]pyrrole-5-carboxylic acid methyl ester (enantiomer B) (1.9 g, 5.0 mmol), hydrazine hydrate (1.2 ml, 25 mmol) and powdered potassium hydroxide (3.4 g, 61 mmol) in dry ethylene glycol (25 ml) was stirred and heated at 100° C. under nitrogen for 16 hours. Upon cooling the mixture was partitioned between dichloromethane and water. The aqueous was further extracted with dichloromethane ) and n-butanol (×2). The combined extracts were evaporated and the residue was purified by chromatography on neutral alumina (grade III) (dry loaded), eluting with CH$_2$Cl$_2$/MeOH/NH$_3$ (95:5:0.5) to give the title amine (1.0 g, 62%) as a pale yellow foam; δ (250 MHz, d$_6$-DMSO) 1.33–1.48 (1H, m), 1.90–2.04 (1H, m), 2.14–2.26 (1H, m), 2.40 (1H, dd, J=11.8, 4.9 Hz), 2.56–2.96 (11H, m), 3.07 (1H, t, J=7.4 Hz), 7.30 (1H, dd, J=8.6, 2.1 Hz, Ar—H), 7.34 (1H, d, J=2.2 Hz, Ar—H), 7.48 (1H, d, J=8.6 Hz, Ar—H), 7.79 (1H, d, J=2.0 Hz, Ar—H), 9.03 (2H, s, Triazole-H), 11.11 (1H, br s, NH).

cis-3-(2-(5-Benzyl-hexahydro-pyrrolo[3,4-b]pyrrol-1-yl)ethyl)-5-[1,2,4]triazol-4-yl-1H-indole. 1.75 Hydrogen oxalate. 0.75 Hydrate (enantiomer B)

Sodium cyanoborohydride (97 mg, 1.5 mmol) was added to a stirred solution of cis-1-(2 -(5-[1,2,4]triazol-4-yl-1H-indol-3-yl)-ethyl)-hexahydro-pyrrolo[3,4-b]pyrrole (enantiomer B) (200 mg, 0.62 mmol) and acetic acid (177 μl, 3.1 mmol) in dry methanol (20 ml) at room temperature under nitrogen. The mixture was then cooled to 0° C., and benzaldehyde (82 μl, 0.81 mmol) was added. The reaction was then allowed to warm slowly to room temperature, and then maintained at this temperature for 16 hours. The reaction was quenched with saturated aqueous potassium carbonate (3 ml). The volatiles were removed in vacuo and the residue was partitioned between dichloromethane and water. The aqueous was further extracted with dichloromethane (×3). The combined extracts were dried (Na$_2$SO$_4$), filtered and evaporated. The residue was purified by chromatography on silica gel, eluting with CH$_2$Cl$_2$/MeOH/NH$_3$ (95:5:0.5→91:8:1) to give the title indole (202 mg, 79%) as a colourless foam. The 1.4 hydrogen oxalate, 0.75 hydrate was prepared (Et$_2$O/MeOH): mp 136–140° C. (Found: C, 58.52; H, 5.96; N, 14.53. C$_{25}$H$_{28}$N$_6$.1.75 (C$_2$H$_2$O$_4$).0.75 (H$_2$O) requires C, 58.65; H, 5.70; N, 14.40%) δ (360 MHz, d$_6$-DMSO) 1.68–1.78 (1H, m), 2.18–2.26 (1H, m), 2.44–2.50 (1H, m), 2.56–2.64 (1H, m), 2.68–2.76 (1H, m), 2.90–3.00 (1H, m), 3.04–3.12 (3H, m), 3.20–3.27 (2H, m), 3.32–3.40 (1H, m), 3.52 (1H, br s), 3.69 (1H, d, J=14.2 Hz, 1 of C$\underline{H}_2$Ph), 3.83 (1H, d, J=14.2 Hz, 1 of C$\underline{H}_2$Ph), 3.90–3.98 (1H, m), 7.26–7.40 (7H, m, Ar—H), 7.52 (1H, d, J=8.5 Hz, Ar—H), 7.84 (1H, s, Ar—H), 9.02 (2H, s, Trazole-H), 11.27 (1H, s, NH).

EXAMPLE 2 cis-3-(2-(5-(Furan-3-yl)methyl-hexahydro-pyrrolo[3, 4-b]pyrrol-1-yl)-ethyl)-5-1,2,4]triazol-4-yl-1H-indole. Bis Hydrogen Oxalate (enantiomer B)

Sodium cyanoborohydride (97 mg, 1.5 mmol) was added to a stirred solution of cis-1-(2-(5-[1,2,4]triazol-4-yl-1H- indol-3-yl)-ethyl)-hexahydro-pyrrolo[3,4-b]pyrrole (enantiomer B) (200 mg, 0.62 mmol) and acetic acid (177 μl, 3.1 mmol) in dry methanol (20 ml) at room temperature under nitrogen. The mixture was then cooled to 0° C. and 3-furaldehyde (70 μl, 0.81 mmol) was added. The reaction was allowed to warm to room temperature and then maintained at this temperature for 16 hours. The reaction was quenched with saturated aqueous potassium carbonate (3 ml). The volatiles were removed in vacuo and the residue was partitioned between dichloromethane and water. The aqueous was further extracted with dichloromethane (×3). The combined extracts were dried ($Na_2SO_4$), filtered and evaporated. The residue was purified by chromatography on silica gel, eluting with $CH_2Cl_2$/MeOH/$NH_3$ (95:5:0.5→91:8:1) to give the title indole (224 mg, 90%) as a colourless foam. The bis hydrogen oxalate was prepared ($Et_2O$/MeOH): mp 136–140° C. (Found: C, 55.43; H, 5.14; N, 14.55. $C_{23}H_{26}N_6O.2(C_2H_2O_4)$ requires C, 55.67; H, 5.19; N, 14.43%) δ (360 MHz, $d_6$-DMSO) 1.64–1.74 (1H, m), 2.14–2.24 (1H, m), 2.51–2.66 (2H, m), 2.76–2.80 (1H, m), 2.88–2.96 (1H, m), 3.02–3.32 (6H, m), 3.38–3.44 (1H, m), 3.60–4.00 (3H, m, partially obscured by HOD), 6.51 (1H, s, Ar—H), 7.34 (1H, dd, J=8.6, 2.1 Hz, Ar—H), 7.38 (1H, d, J=2.1 Hz, Ar—H), 7.52 (1H, d, J=8.6 Hz, Ar—H), 7.63 (1H, s, Ar—H), 7.65 (1H, s, Ar—H), 7.85 (1H, d, J=2.0 Hz, Ar—H), 9.03 (2H, s, Triazole-H), 11.26 (1H, br s, N—H).

EXAMPLE 3 cis-3-(2-(5-Phenylethyl-hexahydro-pyrrolo[3,4-b] pyrrol-1-yl)-ethyl)-5-[1,2,4]triazol-4-yl-1H-indole. 1.5 Hydrogen Oxalate. (enantiomer B)

Sodium cyanoborohydride (97 mg, 1.5 mmol) was added to a stirred solution of cis-1-(2-(5-[1,2,4]triazol-4-yl-1H-indol-3-yl)-ethyl)-hexahydro-pyrrolo[3,4-b]pyrrole (enantiomer B) (200 mg, 0.62 mmol) and acetic acid (177 μl, 3.1 mmol) in dry methanol (20 ml) at room temperature under nitrogen. The mixture was then cooled to 0° C. and phenylacetaldehyde (100 mg, 0.83 mmol) was added. The reaction was then allowed to warm slowly to room temperature, and then maintained at this temperature for 16 hours. The reaction was quenched with saturated aqueous potassium carbonate (3 ml). The volatiles were removed in vacuo and the residue was partitioned between dichloromethane and water. The aqueous was further extracted with dichloromethane (×3). The combined extracts were dried ($MgSO_4$), filtered and evaporated. The residue was purified by chromatography on silica gel, eluting with $CH_2Cl_2$/MeOH/$NH_3$ (95:5:0.5→91:8:1) to give the title indole (141 mg, 53%) as a foam. The 1.5 hydrogen oxalate was prepared ($Et_2O$/MeOH): (Found: C, 62,02; H, 6.33; N, 14.76. $C_{26}H_{30}N_6.1.5(C_2H_2O_4)$ requires C, 62.02; H, 5.92; N, 14.96%). δ (360 MHz, $d_6$-DMSO) 1.64–1.76 (1H, m), 2.14–2.24 (1H, m), 2.72–3.44 (16H, m), 7.20–7.40 (7H, m, Ar—H), 7.52 (1H, d, J=8.6 Hz, Ar—H), 7.84 (1H, d, J=2.0 Hz, Ar—H), 9.03 (2H, s, Triazole-H), 11.25 (1H, br s, N—H).

EXAMPLE 4 cis-3-(2-(5-(4-Fluorobenzyl)-hexahydro-pyrrolo[3,4-b]pyrrol-1-yl)-ethyl)-5-[1,2,4]-triazol-4-yl-1H-indole. 2 Hydrogen oxalate. 0.1 Etherate (enantiomer B)

Sodium cyanoborohydride (66 mg, 1.1 mmol) was added in one portion to a stirred solution of cis-1-(2-(5-[1,2,4] triazol-4-yl-1H-indole-3-yl)-ethyl)-hexahydro-pyrrolo[3,4-b]pyrrole (enantiomer B) (150 mg, 0.47 mmol) and acetic acid (135 μl, 2.4 mmol) in dry methanol (15 ml) at room temperature under nitrogen. The mixture was then cooled to 0° C. and 4-fluorobenzaldehyde (70 μl, 0.65 mmol) was added. After 30 minutes at 0° C. the cooling bath was removed and the reaction stirred at room temperature for 16 hours. The reaction was quenched with saturated aqueous potassium carbonate (5 ml). The volatiles were then removed in vacuo and the residue was partitioned between dichloromethane and water. The aqueous was further extracted with dichloromethane (×3). The combined extracts were dried ($Na_2SO_4$), filtered and evaporated. The residue was purified by chromatography on silica gel, eluting with $CH_2Cl_2$/MeOH/$NH_3$ (91:8:1) to give the title indole (158 mg, 78%) as a colourless foam. The bis hydrogen oxalate 0.1 etherate was prepared ($Et_2O$/MeOH): (Found: C, 57.06; H, 5.40; N, 13.23. $C_{25}H_{27}FN_6.2(C_2H_2O_4)$ 0.1($C_4H_{10}O$) requires C, 57.14; H, 5.22; N, 13.60%) δ (360 MHz, $d_6$-DMSO) 1.68–1.80 (1H, m), 2.18–2.30 (1H, m), 2.40–2.48 (1H, m), 2.54–2.60 (1H, m), 2.70 (1H, d, J=9.0 Hz), 2.92–3.02 (1H, m), 3.06–3.14 (3H, m), 3.20–3.30 (2H, m), 3.34–3.40 (1H, m), 3.50–3.58 (1H, br m), 3.66 (1H, d, J=13.4 Hz, 1 of C$\underline{H}_2$Ar), 3.77 (1H, d, J=13.2 Hz, 1 of C$\underline{H}_2$Ar), 3.94–4.00 (1H, m), 7.13–7.18 (2H, m, ArH), 7.33–7.43 (3H, m, ArH), 7.52 (1H, d, J=8.6 Hz, ArH), 7.87 (1H, d, J=1.9 Hz), 9.03 (2H, s, Triazole-H), 11.29 (1H, br s, N—H).

EXAMPLE 5 cis-3-(2-(5-(2,4-Difluorobenzyl)hexahydro-pyrrolo [3,4-b]pyrrol-1-yl)-ethyl)-5-[1,2,4]-triazole-4-yl-1H-indole. 1.5 Hydrogen oxalate. 0.1 Hydrate. 0.2 Etherate (enantiomer B)

Sodium cyanoborohydride (66 mg, 1.1 mmol) was added in one portion to a stirred solution of cis-1-(2-(5-[1,2,4] triazol-4-yl-1H-indol-3-yl)ethyl)-hexahydro-pyrrolo[3,4-b] pyrrole (enantiomer B) (150 mg, 0.47 mmol) and acetic acid (135 μl, 2.4 mmol) in dry methanol (15 ml) at room temperature under nitrogen. The mixture was then cooled to 0° C. and 2,4-difluorobenzaldehyde (66 μl, 0.60 mmol) was added. After 30 minutes the ice bath was removed and the reaction stirred at room temperature for 16 hours. The reaction was quenched with saturated aqueous potassium carbonate (5 ml). The volatiles were then removed in vacuo. The residue was partitioned between dichloromethane and water. The aqueous was further extracted with dichloromethane (×2). The combined extracts were washed with brine (×1), then dried ($Na_2SO_4$), filtered and evaporated. The residue was purified by chromatography on silica gel eluting with $CH_2Cl_2$/MeOH/$NH_3$ (91:8:1) to give the title indole (136 mg, 65%) as a colourless foam. The 1.5 hydrogen oxalate. 0.1 hydrate 0.2 etherate was prepared ($Et_2O$/MeOH): (Found: C, 57.89; H, 5.57; N, 13.66. $C_{25}H_{26}F_2N_6.1.5(C_2H_2O_4).0.2(C_4H_{10}O).0.1(H_2O)$ requires C, 57.63; H, 5.24; N, 14.00%) δ (360 MHz, $d_6$-DMSO) 1.68–2.00 (1H, m), 2.20–2.30 (1H, m), 2.34–2.40 (1H, m), 2.46–2.52 (1H, m), 2.66–2.70 (1H, m), 2.90–2.98 (1H, m), 3.08–3.22 (4H, m), 3.28–3.42 (2H, m), 3.50–3.60 (1H, br m), 3.69 (2H, br s, C$\underline{H}_2$Ar), 4.00–4.06 (1H, m), 7.07 (1H, br t, J=8.5 Hz, ArH), 7.20 (1H, br t, J=9.9 Hz, ArH), 7.33–7.38 (2H, m, ArH), 7.51–7.55 (2H, m, Ar—H), 7.88 (1H, d, J=2.0 Hz, ArH), 9.03 (2H, s, triazole H), 11.30 (1H, br s, NH).

I claim:
1. A compound of formula I, or a salt thereof:

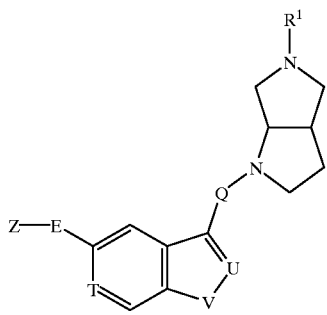

(I)

wherein
- Z represents 1,2,4-triazole optionally substituted with $C_{1-6}$ alkyl, $C_{2-6}$ alkenyl, $C_{2-6}$ alkynyl, $C_{3-7}$ cycloalkyl, aryl, aryl($C_{1-6}$)alkyl, $C_{1-6}$ alkoxy, $C_{1-6}$ alkylthio, amino, $C_{1-6}$ alkylamino, di($C_{1-6}$)alkylamino, halogen, cyano or trifluoromethyl, wherein aryl represents phenyl or naphthyl
- E represents a chemical bond or a straight or branched alkylene chain containing from 1 to 4 carbon atoms;
- Q represents a straight or branched alkylene chain containing from 1 to 6 carbon atoms, optionally substituted in any position by a hydroxy group;
- T represents CH;
- U represents C—$R^2$;
- V represents N—$R^3$;
- $R^1$ represents $C_{3-6}$ alkenyl, $C_{3-6}$ alkynyl, or aryl($C_{1-6}$) alkyl, wherein aryl is phenyl or naphthyl, any of which groups may be optionally substituted with one or more substituents selected from halogen, cyano, $C_{1-6}$ alkoxy, amino, di($C_{1-6}$)alkylamino, di($C_{1-6}$)alkylaminomethyl, $C_{2-6}$ alkylcarbonylaminio, $C_{2-6}$ alkoxycarbonylaminio, N-($C_{1-6}$)alkyl-N-($C_{2-6}$)alkoxycarbonylamino, $C_{1-6}$ alkylsulphonylamino, aminocarbonylamino, aminocarbonyl, $C_{1-6}$ alkylaminocarbonyl, di($C_{1-6}$) alkylaminocarbonyl, aminosulphonyl and $C_{1-6}$ alkylaminosulphonylmethyl; and
- $R^2$ and $R^3$ independently represent hydrogen or $C_{1-6}$ alkyl.

2. A compound as claimed in claim 1 represented by formula IIA, or a salt thereof:

(IIA)

wherein

- m is zero, 1, 2 or 3;
- p is 1, 2 or 3;
- $Q^1$ represents a straight or branched alkylene chain containing from 2 to 5 carbon atoms, optionally substituted in any position by a hydroxy group;
- T represents CH;
- A represents nitrogen and B represents C—$R^8$, or B represents nitrogen and A represents CH;
- $R^7$ and $R^8$ independently represent hydrogen, $C_{1-6}$ alkyl, $C_{2-6}$ alkenyl, $C_{3-7}$ cycloalkyl, aryl, aryl($C_{1-6}$)alkyl, $C_{1-6}$ alkoxy, $C_{1-6}$ alkylthio, amino, $C_{1-6}$ alkylamino, di($C_{1-6}$)alkylamino, halogen, cyano or trifluoromethyl, wherein aryl represents phenyl or naphthyl; and
- W represents a group of formula (Wa):

(Wa)

in which
- $W^1$ represents CH;
- $R^9$ represents hydrogen, halogen, cyano, trifluoromethyl, $C_{1-6}$ alkoxy, $C_{2-6}$ alkylcarbonyl, amino, $C_{1-6}$ alkylamino, di($C_{1-6}$)alkylamino, di($C_{1-6}$)alkylaminomethyl, $C_{2-6}$ alkylcarbonylamino, $C_{1-6}$ alkylsulphonylamino, aminocarbonylamino, $C_{1-6}$ alkylaminocarbonyl, aminosulphonyl or $C_{1-6}$ alkylaminosulphonylmethyl; and
- $R^{10}$ represents hydrogen or halogen.

3. A method for the treatment of migraine and associated conditions, which method comprises administering to a patient in need of such treatment an effective amount of a compound as claimed in claim 1.

4. A method for the treatment of migraine and associated conditions as recited in claim 3, wherein said associated conditions are selected from the group consisting of cluster headache, chronic paroxysmal hemicrania, headache associated with vascular disorders, tension headache, and pediatric migraine.

5. A compound selected from:
- 7-benzyl-2-[2-(5-(1,2,4-triazol-4-yl)-1H-indol-3-yl) ethyl]-cis-2,7-diazabicyclo[3.3.0]octane;
- 7-(2-phenylethyl)-2-[2-(5-(1,2,4-triazol-4-yl)-1H-indol-3-yl)ethyl]-cis-2,7-diazabicyclo[3.3.0]octane;
- 7-(4-fluorobenzyl)-2-[2-(5-(1,2,4-triazol-4-yl)-1H-indol-3-yl)ethyl]-cis-2,7-diazabicyclo[3.3.0]octane;
- 7-(2,4-difluorobenzyl)-2-[2-(5-( 1,2,4-triazol-4-yl)-1H-indol-3-yl)ethyl]-cis-2,7-diazabicyclo[3.3.0]octane;

or a salt thereof.

* * * * *